United States Patent
Bicker et al.

(10) Patent No.: US 6,915,680 B2
(45) Date of Patent: Jul. 12, 2005

(54) METHOD AND SYSTEM FOR DETERMINING SURFACE TENSION USING THE BUBBLE PRESSURE METHOD

(75) Inventors: Rainer Bicker, Guetersloh (DE); Michael Finke, Hoevelhof (DE); Helge Mueller, Guetersloh (DE)

(73) Assignee: Miele & Cie. KG, Guetersloh (DE)

( * ) Notice: Subject to any disclaimer, the term of this patent is extended or adjusted under 35 U.S.C. 154(b) by 0 days.

(21) Appl. No.: 10/786,492

(22) Filed: Feb. 25, 2004

(65) Prior Publication Data

US 2004/0163447 A1 Aug. 26, 2004

(30) Foreign Application Priority Data

Feb. 25, 2003 (DE) .......................... 103 08 198

(51) Int. Cl.⁷ .............................................. G01N 13/00
(52) U.S. Cl. ..................................... 73/64.48; 73/64.51
(58) Field of Search ........................... 73/64.48, 64.51, 73/64.49

(56) References Cited

U.S. PATENT DOCUMENTS 5,404,606 A  *  4/1995  Mueller-Kirschbaum et al. .............................. 8/158

FOREIGN PATENT DOCUMENTS

| DE | 4112417 | 10/1992 | |
|---|---|---|---|
| DE | 19529787 | 2/1997 | |
| DE | 19653752 A1 * | 6/1998 | .......... G01N/13/02 |
| DE | 19819555 | 11/1999 | |
| DE | 10025430 | 12/2000 | |
| DE | 10029505 A1 * | 12/2000 | .......... G01N/13/02 |
| DE | 10022863 | 11/2001 | |
| DE | 10110213 | 9/2002 | |
| EP | 760472 A2 * | 3/1997 | .......... G01N/13/02 |
| EP | 1154255 A2 * | 11/2001 | .......... G01N/13/02 |
| GB | 2265222 A * | 9/1993 | .......... G01N/13/02 |

* cited by examiner

*Primary Examiner*—Hezron Williams
*Assistant Examiner*—Tamiko Bellamy
(74) *Attorney, Agent, or Firm*—Davidson, Davidson & Kappel, LLC (57) ABSTRACT

A method for determining a surface tension of a solution in a container using a bubble pressure process includes introducing a gas volume flow into the solution using a capillary. A time-dependent pressure profile of the gas volume flow is determined during bubble formation using a pressure sensor. The gas volume flow is interrupted toward the end of the determination process by closing the capillary over the entire cross section of the capillary over at least a part of the length of the capillary.

16 Claims, 6 Drawing Sheets

METHOD AND SYSTEM FOR DETERMINING SURFACE TENSION USING THE BUBBLE PRESSURE METHOD

Priority is claimed to German patent application DE 103 08 198.4-52, the subject matter of which is hereby incorporated by reference herein.

The present invention relates to a method for determining the surface tension of a solution contained in a container, in particular a surfactant solution, according to the bubble pressure method, using a capillary for introducing a gas volume flow into the solution as well as a pressure sensor for determining the time-dependent pressure profile of this volume flow during bubble formation. Moreover, the present invention relates to a system for carrying out such a method.

BACKGROUND

A method and a system for determining the surface tension of a solution contained in a container are known, for example, from German Patent Application DE 100 22 863 A1.

The measurement of the dynamic surface tension according to the bubble pressure method is based on the dependence of the surface tension on the pressure during the formation of curved surfaces. It is known, for example, from German Patent Applications DE 41 12 417 A1 and DE 195 29 787 A1, to determine the detergent concentration of a detergent/water mixture (washing liquid, for example, in the soapy water container of a washing machine) by measuring the surface tension. In this context, the bubble pressure method has the advantage that the surface tension can be determined (dynamically) at surfaces of different age. The slower a bubble is formed, the more time the surfactants have to get to the surface and to reduce the surface tension. This velocity of the surfactants is also determined in this method (see DE 100 29 505 A1).

In the bubble pressure method, a continuously supplied airflow creates a bubble in the washing liquid at a capillary. The differential pressure between the forming and the detaching bubble is then proportional to the surface tension. In order to create the bubbles, a gaseous medium, generally air, is introduced through a narrow capillary tube into the washing liquid to be sensed. If this capillary tube is arranged directly in the soapy water container, then there is a risk for the capillary orifice to become clogged by dirt particles after some time. This problem is increased if the gas bubbles are created by a pump, and if this pump is switched off after the measuring process when the soapy water container is full. Then, liquid flows into the capillary and further into the hose to which the capillary is connected. If a deposit of lime or dirt forms in this hose and comes off later, the detached particles are blown by the pump into the capillary, clogging the capillary. In order to avoid this, German Patent Application DE 100 25 430 A1 proposes that the capillary for measuring the surface tension in a washing machine be accommodated in a vessel which is located in the wall of the soapy water container and filled by scooping devices on the washing drum. In addition, the intention is for the vessel to be regularly cleaned by inflowing water. The imbalance during spinning is used to empty the vessel. In this context, it is a disadvantage that the emptying of the vessel by the imbalance cannot be carried out in a defined manner because the imbalance occurring during spinning is sometimes greater and sometimes less. In addition, it is necessary to attach a scooping device to the washing drum, which is not easy to accomplish for reasons of space.

From German Patent Application DE 100 22 863 A1, it is known for the capillary to open into a measuring chamber, in which a column of liquid that rises above the level of the outlet of the capillary can be produced by negative pressure. This ensures that the gas flow in the capillary is always in the direction of the liquid-filled measuring chamber. The intention of this is that the risk of clogging should be low; however, small amounts of liquid are nevertheless drawn into the capillary because of the capillary effect and due to negative pressure in the measuring chamber caused by cooling. Small amounts of liquid already lead to the formation of additional air/liquid interfaces inside the measuring chamber and interfere with the measurement. A cleaning operation (piercing, known from German Patent Application DE 195 29 787 A1) would now indeed allow the geometry of the orifice to be retained and would prevent it from being clogged by deposits. However, this cannot prevent ingress of liquid into the measuring chamber either.

German Patent Application DE 196 53 752 A1 describes a method and device for cleansing process measuring cells containing capillaries, using a combination of ultrasound in conjunction with a flow of cleaning gas and liquid. A device of this type is too expensive for broad application in domestic appliances such as washing machines and dishwashers.

SUMMARY OF THE INVENTION

It is therefore an object of the present invention to provide a method and system of the type mentioned at the outset for determining the surface tension which reliably prevents contamination of the capillary with little effort.

The present invention provides a method for determining the surface tension of a solution contained in a container, in particular a surfactant solution, according to the bubble pressure method, using a capillary for introducing a gas volume flow into the solution as well as a pressure sensor for determining the time-dependent pressure profile of this volume flow during bubble formation. According to the method of the present invention, towards the end of the determination process, the volume flow is interrupted by closing the capillary over its entire cross section at least over part of its length.

The present invention also provides a system for carrying out a method for determining the surface tension of a solution contained in a container, in particular a surfactant solution, according to the bubble pressure method, using a capillary for introducing a gas volume flow into the solution as well as a pressure sensor for determining the time-dependent pressure profile of this volume flow during bubble formation. The system includes a closing device for the capillary, the closing device being movable from a measuring position to a locking position in which the capillary is sealed from the solution in a liquid-tight manner.

A particular advantage that can be achieved with the present invention is that contamination of the capillary is not removed posteriorly, but prevented even before it occurs.

In a convenient embodiment of the system according to the present invention, the closing device is operated by a control device which is in communication with the evaluation circuit for determining the time-dependent pressure profile of the volume flow.

In one advantageous embodiment of the system, the length of the capillary is at most half its diameter. In this manner, it is possible for the initial curvature of the bubble to be sufficiently small for reliable detection of the point of minimum pressure, even in the case of a capillary wall that is highly wettable due to deposits.

It is advantageous if the capillary has a first outlet opening directed toward the solution, and a second opening which opens into a measuring chamber, and if the closing device has a cleaning needle which can be moved into the second opening from the measuring chamber. This provides additional cleaning of deposits that have formed on the inner wall of the capillary in spite of the closure of the capillary. In such a system, in particular, it is advantageous for the cleaning needle to be surrounded by a seal which, when the closing device is in the locking position, makes contact with the wall of the measuring chamber into which the capillary opens. In this manner, the capillary is reliably closed. In convenient embodiments, the closing device can be moved pneumatically or electromagnetically in a simple manner.

In an alternative embodiment of the system, the capillary is designed as a bore located in first ceramic disk, and the closing device includes a second ceramic disk having an opening that can be moved in front of the capillary in the measuring position of the closing device. Using the ceramic disks it is possible to obtain extremely high levels of sealing performance as are known from sanitary applications. In a convenient embodiment, the second ceramic disk is located on the side of the capillary facing the solution. Furthermore, it is advantageous if the capillary is cleaned and additionally closed by a cleaning element that can be inserted into the orifice opposite the solution. It is also convenient to move the second ceramic disk and/or the cleaning element electromotively, electromagnetically, by a piezoelectric actuator, or a memory metal.

BRIEF DESCRIPTION OF THE DRAWINGS

Exemplary embodiments of the present invention are shown schematically in the drawings and will be described in more detail below.

DETAILED DESCRIPTION

Figure 1A:
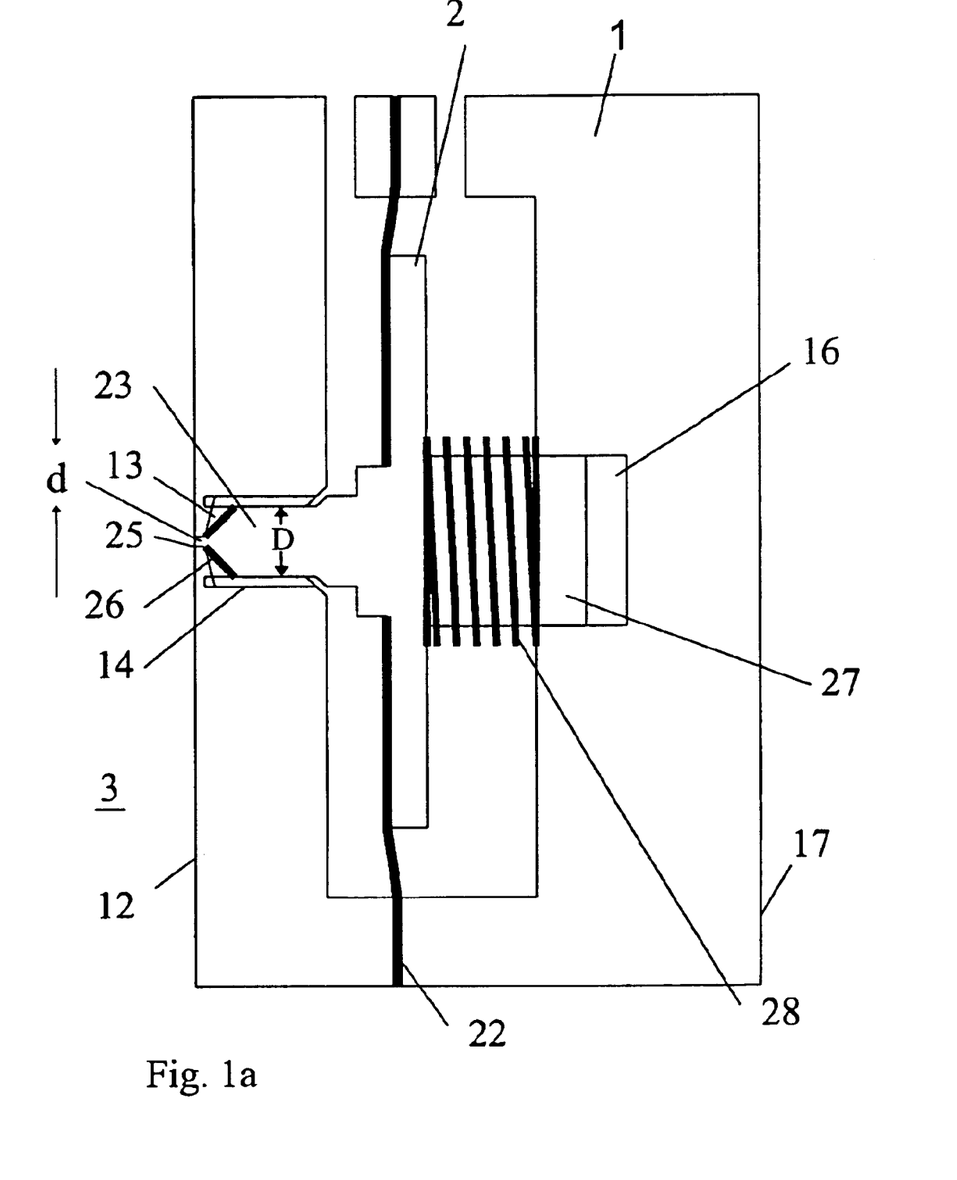
FIGS. 1a,b show the capillary unit of a system for determining the surface tension with the closing device (2) in the locking position (FIG. 1a) and in the measuring position (FIG. 1b).
Figure 1B:
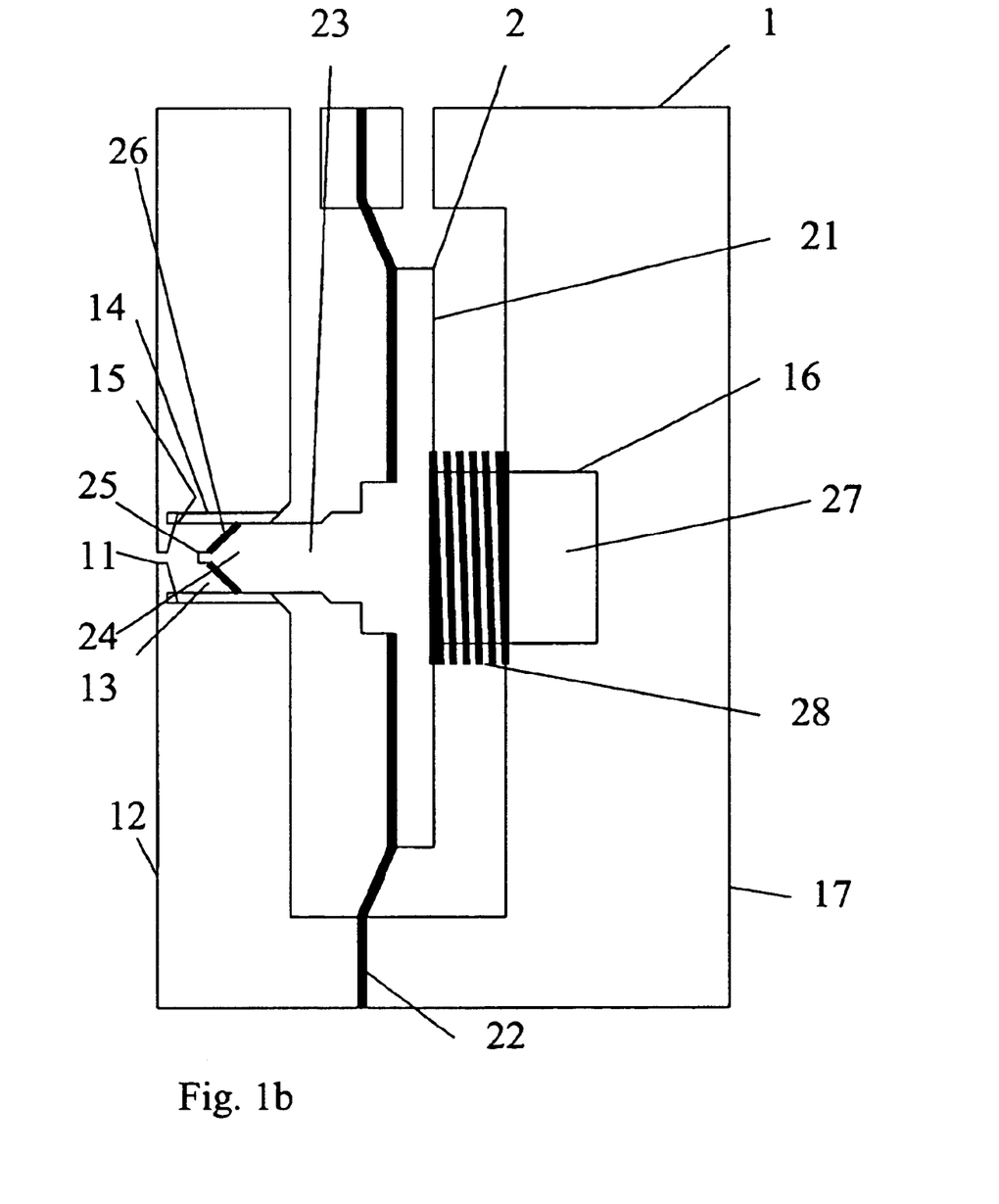

FIG. 1a and 1b show the general design of a capillary unit, including closing device (2), in a sectional view. This unit is used in the system according to FIG. 2. The systems shown in FIGS. 3 and 4 differ from the system according to FIG. 2 with respect to the operation of closing device (2), which is why closing device (2) in each case needs to be slightly modified. In each of the exemplary embodiments, the systems form part of a washing machine and are used for determining the surface tension of soapy wash water (3) in the soapy water container of this machine.

The system includes a chamber (1) that is closed except for the capillary and one or more inlet openings. The soapy wash water (3) is in front of left chamber wall (12). This chamber wall (12) is provided with a cylindrical blind hole (13) which has a diameter D and a tapered end. The walls of the blind hole are widened by narrow channels (14) whose function will be explained later. A through-bore having a smaller diameter d extends from the tip of blind hole (13) through the chamber wall, and forms the actual capillary (11). Therefore, capillary (11) can be regarded as a short tube which has a first outlet directed toward soapy wash water (3), and a second outlet directed toward chamber (1). The depth of blind hole (13) is dimensioned in such a way that the length of capillary (11) is smaller than its diameter d.

Located in chamber (1) is a closing device (2) having a disk-shaped base (21) that is attached to the chamber wall in such a manner that it can move in an axial direction. Depending on the operating device, the attachment arrangement is designed as a membrane (22) (in the case of a pneumatic drive), or as a guide (in case of an electromagnetic drive, not shown). Base (21) has an integrally formed plunger (23) on the side facing capillary (11). The plunger is cylindrical in shape and sized in diameter such that it can be guided in blind hole (13) with a small clearance. The tip of plunger (23) changes from a conical portion (24) into a cleaning needle (25) which has about the diameter d of capillary (11). Conical portion (24) carries a seal (26) which makes contact with the conical surface (15) of blind hole (13) in the locking position, thus closing capillary (11) in an airtight and liquid-tight manner. The back side of base (21) changes into a cylindrical extension (27), which is guided in a bore (16) in rear chamber wall (17). Extension (27) is surrounded by a coil spring (28) which is braced against base (21) on one side and against chamber wall (17) on the other side. It is also possible to provide an electromagnetic drive (see FIG. 3).

In FIG. 1a, closing device (2) is in the locking position. Cleaning needle (25) then fills capillary (11), thus ensuring that its geometry is retained. The purpose of seal (26) is to close capillary (11) on the inside of the chamber so as to reliably prevent ingress of soapy wash water (3) into capillary (11). The required contact pressure is provided by spring (28). FIG. 1b shows the measuring position. Closing device (2) is operated by negative pressure in the right chamber half. The negative pressure acts upon membrane (22), which pulls cleaning needle (25) out of capillary (11). In the process, seal (26) clears conical surface (15) of blind hole (13). In this position, air can be conveyed from chamber (1) through channels (14), and then further through capillary (11) so that bubbles are created in soapy wash water (3).

Figure 2:
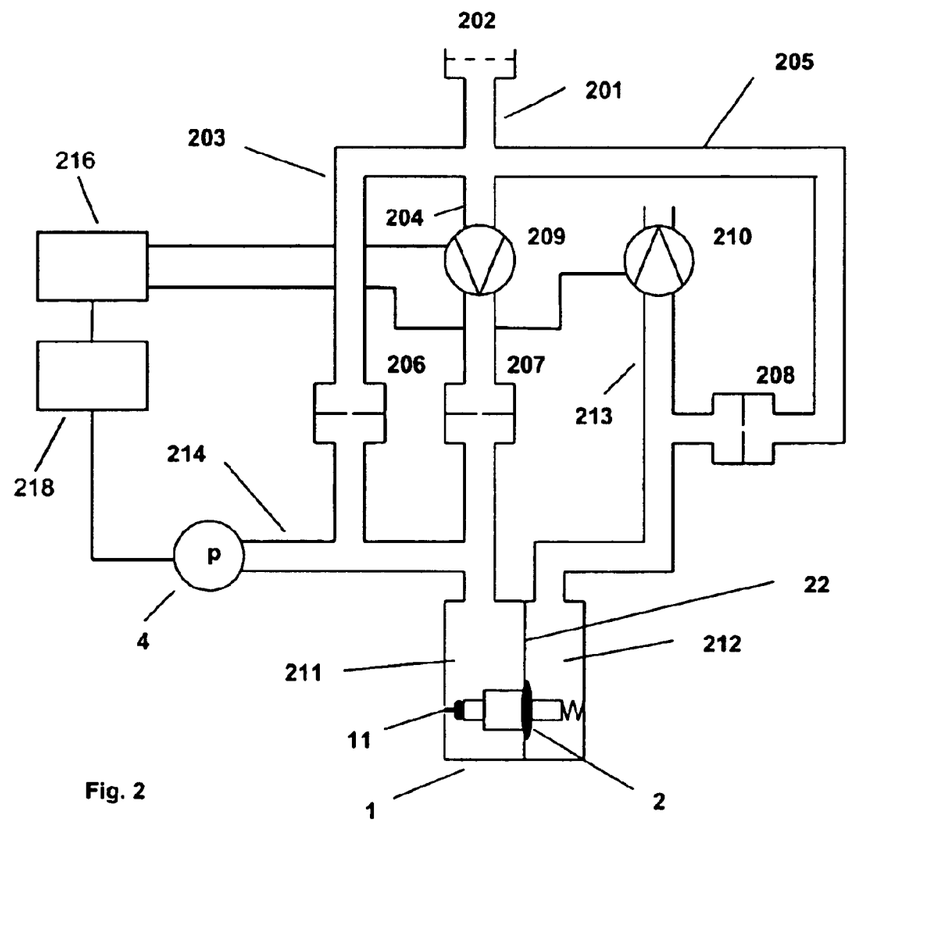
FIG. 2 shows a schematic diagram of a system for determining the surface tension which has a pneumatically moved closing device (2) and uses two pumps (209, 210).

The function of the overall system is shown in FIG. 2:

An open supply line (201) is in communication with the ambient air; a filter (202) removing any dirt that might be present in the air. Downstream of filter (202), supply line (201) branches into three lines (203, 204, 205), which each have a throttle (206, 207, 208) installed therein. Downstream of throttle (206), a line (214) having a pressure sensor (4) connected to its end branches off from line (203). In central line (204), a pump (209), whose suction side is associated with the opening of supply line (201) and whose pressure side is associated with throttle (207), is connected upstream of throttle (207). The two lines (203) and (204) are routed into the left side (211) of the chamber. The right line (205) opens into the right side (212) of chamber (1). Upstream of the outlet, a line (213) branches off, in which a further pump (210) is arranged. This pump (210) is in communication with chamber side (212) on the suction side. Pump (209) is used to create the bubbles. A positive pressure, which is supplied to capillary (11), is generated in line (203) between pump (209) and throttle (207). Pump (210) is used to move closing device (2), thus clearing the capillary. Both pumps (209, 210) are supplied with power via a control device (216), which is in communication with an evaluation circuit (218) for evaluating the pressure profile over time. The control device 216 and the evaluation circuit 218 can be integrated into a microprocessor control of the washing machine.

The procedure is as follows:

First, pump (209) is switched on. In this manner, a positive pressure is generated which is also transmitted to membrane (22) of closing device (2) via throttle (207). This results in a "fluttering" opening, involving the emergence of bubbles. However, measurement is not possible at this stage because the high pressure required to operate the membrane must be built up and sensed. The pressure of the bubble does not reach pressure sensor (4). Now, pump (210) is switched on as well. Because of this, negative pressure is generated in right chamber half (212) on the back side of membrane (22) so that closing device (2) is pulled out of capillary (11), and also kept pulled out by this negative pressure. Then, the pump (209) is switched off, and the measurement is carried out by pressure sensor (4), starting with the highest initial bubble frequency (for example, 20 Hz) into the measuring range (10 Hz . . . 1 Hz). When the bubble frequency drops below the minimum of 1 Hz, pump (209) is switched on again to reliably prevent ingress of soapy wash water (3), since throttle (206) constitutes a vent to the outside. Then, pump (210) is switched off so that the negative pressure in right chamber half (212) is removed to the ambient environment via throttle (208), moving closing device (2) into capillary (11). After the closure of capillary (11), pump (209) is switched off as well, and ambient pressure gradually builds up at pressure sensor (4) again by venting through throttle (206).

Figure 3:
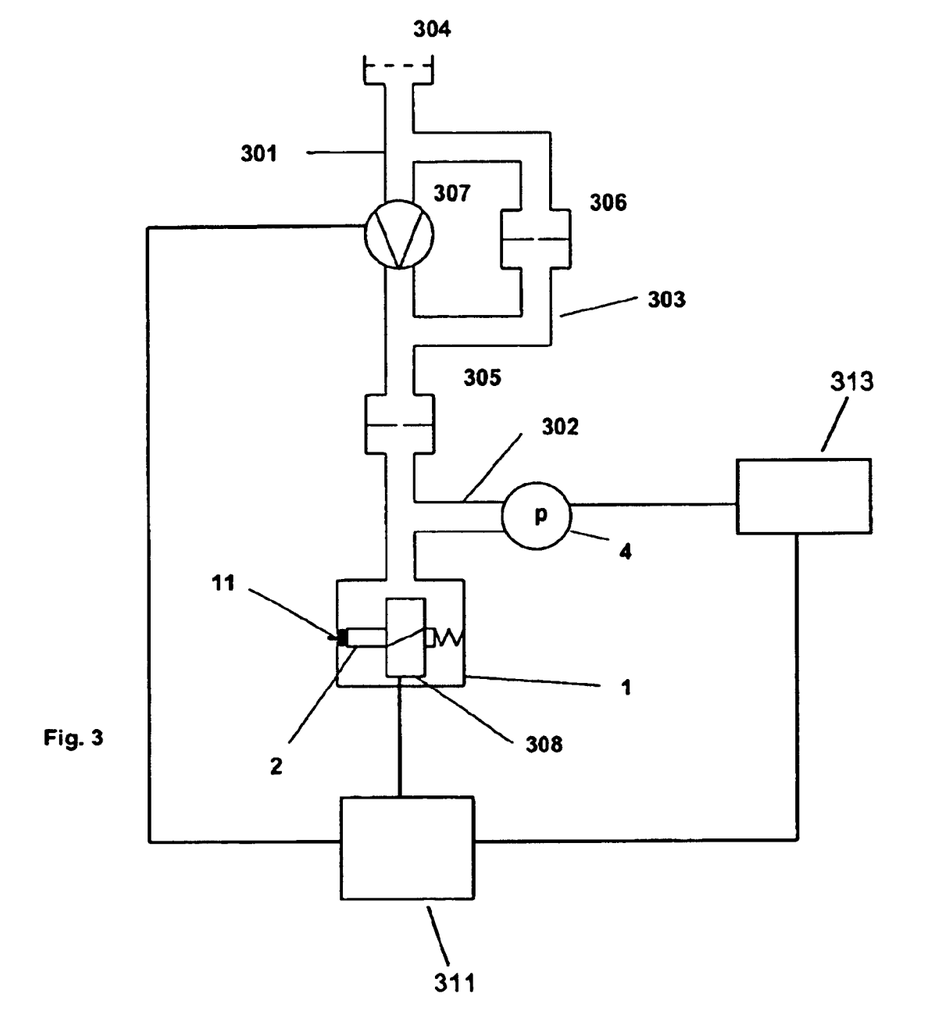
FIG. 3 shows a schematic diagram of a system for determining the surface tension which has an electromagnetically moved closing device (2).

FIG. 3 shows a system in which closing device (2) is moved by an electromagnet. As in the previous variant, the capillary orifice is cleaned and sealed by a plunger (23) having a cleaning needle (25) and a seal (26). Here too, a line (301) is in communication with the ambient air via an interposed filter (304). Located in line (301) is a pump (307) whose suction side is associated with the opening of the line, and whose pressure side is associated with a downstream throttle (305). Downstream of throttle (305), a line (302) that is terminated by pressure sensor (4) branches off from line (301). A throttle (306) is connected in parallel with pump (307) via a line (303). Line (301) opens into the chamber. Pump (307) is supplied with power via a control device (311), which is used to operate a solenoid (308) of the electromagnet, and which is in communication with an evaluation circuit (313) for evaluating the pressure profile over time.

The procedure is as follows:

Pump (307) draws in air through filter (304), and compresses the air in the section of line (301) between pump (307) and throttle (305). This high pressure is transmitted via throttle (305) into chamber (1) and thus to the region of capillary (11), and can be measured at pressure sensor (4). Then, closing device (2) is pulled out of capillary (11) by energizing the solenoid (308) of the electromagnet via the control device (311). In the process, first, part of the positive pressure in the region between throttle (305) and capillary (11) is removed in that the compressed air escapes through capillary (11) into soapy wash water (3). During this process, a great number of bubbles form in soapy wash water (3) for a short period of time. Then, the actual measurement starts. Pump (307) is switched off, and the pressure existing between pump (307) and throttle (305) pressure gradually decreases. Accordingly, the different bubble frequencies are passed through for the measurement with pressure sensor (4) (starting with the highest bubble frequency). When the bubble frequency drops below the minimum of 1 Hz, solenoid (308) is de-energized so that closing device (2) closes capillary (11) again. Via throttles (305) and (306), the ambient pressure gradually builds up at pressure sensor (4) again.

Figure 4:
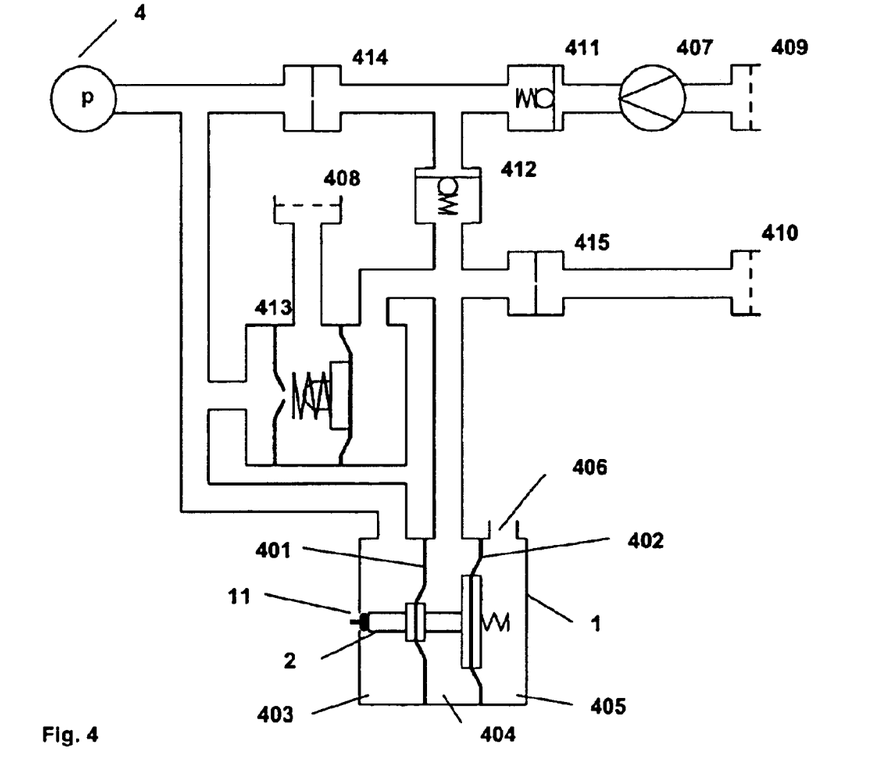
FIG. 4 shows a schematic diagram of a system for determining the surface tension which has a pneumatically moved closing device and uses a pump (407) and a valve control system.

FIG. 4 shows a system in which both the compressed air supply to capillary (11) and the operation of closing device (2) are implemented using a single pump (407). To this end, closing device (2) is attached to two membranes (401, 402), which divide chamber (1) into three chamber sections (403, 404, 405). Each chamber section (403, 404, 405) has a supply line; the line to right chamber section (405) being in direct communication with the ambient air 406. The only active part of this system is pump (407), which is used to compress air for the formation of bubbles, and for all control functions. Pump (407) draws in air through the filter (for better clarity, the filter is shown as 3 filters 408, 409, 410). The air is pressed through valve (411) into the line section between valve (411), valve (412), and throttle (414). From here, it passes on into left chamber region (403) via throttle (414). There, the air escapes through open valve (413) without resistance. A positive pressure builds up in parallel via valve (412) and reaches central chamber region (404). Once a certain pressure (for example, 30 mbar) is exceeded in this region, valve (413) closes. If the pressure increases further (for example, above 80 mbar), closing device (2) is pulled out of capillary (11). In order for the pressure in the region of capillary (11) to play as small a role as possible in the operation of closing device (2), the effective area of membrane (401), which is drawn on the left of the figure, is much larger than the effective area of membrane (402), Which is drawn to the right. After valve (413) closes, the pressure in left chamber region (403) increases and bubbles emerge from capillary (11) as soon as closing device (2) is opened.

After that, pump (407) remains switched on for a while in order for the pressure in the area of central chamber region (404) to increase further to about 200 mbar. Then, pump is switched off.

Now, 2 volumes serving as pressure accumulators need to be considered: On the one hand, the volume between valve (411), valve (412), and throttle (414), which serves as an air reservoir for the formation of bubbles (hereinafter referred to as "compression volume for bubble formation") and, on the other hand, the volume between valve (412), throttle (415), valve (413) and chamber section (404), which receives the pressure for the operation of the different elements (hereinafter referred to as "control volume"). Now, air escapes from both volumes The air from the compression volume escapes through throttle (414) and is used for bubble formation. Air from the control volume escapes in parallel through throttle (415) and (via filter 410) into the environment. The system must be designed such that throttle (415) offers greater resistance to the air than throttle (414). Consequently, the pressure in the compression volume for bubble formation decreases faster than in the control volume.

In this manner, it is possible to generate the different bubble frequencies (starting with the highest) for the measurement as the pressure decreases in the compression volume for bubble formation. The pressure in the control volume decreases in parallel, but this occurs more slowly. Throttle (415) is designed in such a manner that the pressure in the control volume decreases to a level at which closing device (2) closes capillary (11) again only after the bubble frequency has dropped below the minimum. If the pressure decreases further, valve (413) is also reopened, as a result of which pressure sensor (4) is at ambient pressure again.

Figure 5:
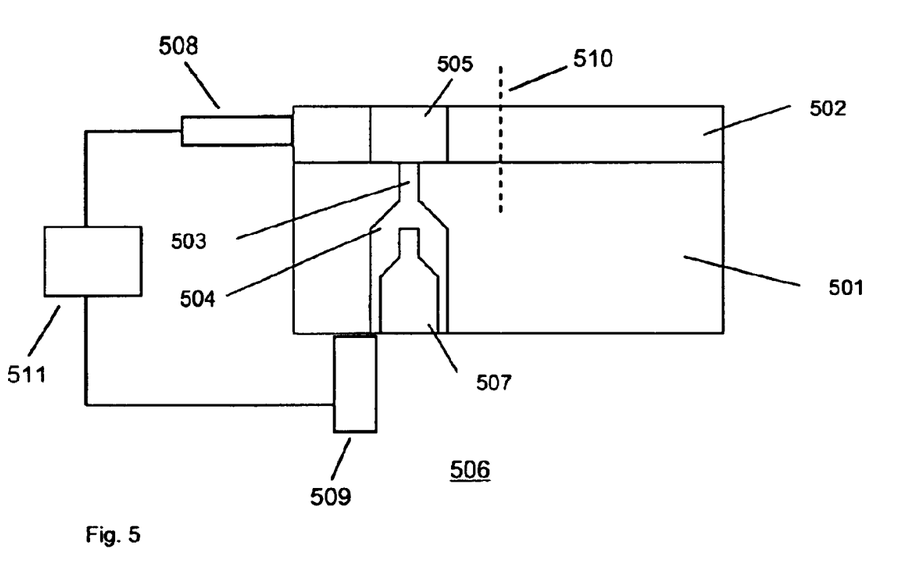
FIG. 5 shows a section through a capillary unit made of ceramic disks.

FIG. 5 is a detail showing a capillary unit in which both the capillary and the closing device are made of ceramic disks (501, 502). The figure shows the schematic design in a sectional view. The two disks (501, 502) have the same diameter and are arranged one above the other. Capillary orifice (503) is provided in first disk (501) as a bore, and is widened by a blind hole (504) of larger diameter on chamber side (506). Second disk (502) is provided with an opening (505) which can be placed in front of capillary orifice (503) by rotating the disk about axis (510), and which thus clears the orifice. A cleaning element (507) which corresponds to the geometry of the capillary orifice, including the widened portion, can be inserted into blind hole (504) from chamber side (506). Second disk (502) and cleaning element (507) can each be moved by a respective drive mechanism 508, 509, which may respectively be an electromotive drive mechanism, an electromagnetic drive mechanism, a piezo-electric actuator, or a memory metal. Control device 511, which is in communication with an evaluation circuit, such as evaluation circuit 313 shown in FIG. 3, controls second disk (502) and cleaning element (507). In the measuring position, capillary orifice (503) is located in the region of opening (505) of second disk (502), and therefore comes into contact with soapy wash water (3), whereas in the locking position, it is covered by the unperforated region of second disk (502), and therefore does not come into contact with soapy wash water (3). In this context, sealing is accomplished by the accurately plane surfaces of ceramic disks (501, 502).

What is claimed is:

1. A method for determining a surface tension of a solution in a container using a bubble pressure process, the method comprising:

introducing a gas volume flow into the solution using a capillary;

determining a time-dependent pressure profile of the gas volume flow during a bubble formation using a pressure sensor;

interrupting the gas volume flow during a latter portion of the determining by closing the capillary over an entire cross section of the capillary over at least a part of a length of the capillary.

2. The method as recited in claim 1 wherein the solution is a surfactant solution.

3. A system for determining a surface tension of a solution in a container using a bubble pressure process, the system comprising:

a capillary configured to introduce a gas volume flow into the solution;

a pressure sensor configured to determine a time-dependent pressure profile of the gas volume flow during a bubble formation;

a closing device for the capillary, the closing device being movable from a measuring position to a locking position, wherein in the locking position the capillary is sealed from the solution in a liquid-tight manner.

4. The system as recited in claim 3 wherein the solution is a surfactant solution.

5. The system as recited in claim 3 further comprising an evaluation circuit configured to determine the time-dependent pressure profile of the gas volume flow; and a control device configured to operate the closing device and being in communication with the evaluation circuit.

6. The system as recited in claim 3 wherein a length of the capillary is at most half a diameter of the capillary.

7. The system as recited in claim 3 wherein:

the capillary has a first outlet directed toward the solution and a second outlet opening into a chamber; and the closing device includes a cleaning needle configured to be moved into the capillary from inside the chamber.

8. The system as recited in claim 7 further comprising a seal encircling the cleaning needle, the seal being configured to contact a wall of the chamber when the closing device is in the locking position.

9. The system as recited in claim 6 wherein the closing device is movable pneumatically.

10. The system as recited in claim 7 wherein the closing device is movable pneumatically.

11. The system as recited in claim 6 wherein the closing device is movable electromagnetically.

12. The system as recited in claim 7 wherein the closing device is movable electromagnetically.

13. The system as recited in claim 3 wherein the capillary includes a bore disposed in a first ceramic disk and wherein the closing device includes a second ceramic disk having an opening, the opening being movable in front of the capillary in a measuring position of the closing device.

14. The system as recited in claim 13 wherein the second ceramic disk is disposed on a side of the capillary facing the solution.

15. The system as recited in claim 14 further comprising a cleaning element insertable into an orifice of the capillary opposite the solution.

16. The system as recited in claim 14 wherein at least one of the second ceramic disk and the cleaning element are movable by at least one of an electromotive drive device, an electromagnetic drive device, a piezoelectric actuator, and a memory metal.

* * * * *